United States Patent
Avery

(10) Patent No.: US 9,180,251 B2
(45) Date of Patent: Nov. 10, 2015

(54) CODED CARTRIDGE ASSEMBLY

(75) Inventor: Richard James Vincent Avery, Chipping Campdem (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 306 days.

(21) Appl. No.: 13/642,077

(22) PCT Filed: Apr. 21, 2011

(86) PCT No.: PCT/EP2011/056482
§ 371 (c)(1),
(2), (4) Date: Dec. 21, 2012

(87) PCT Pub. No.: WO2011/131783
PCT Pub. Date: Oct. 27, 2011

(65) Prior Publication Data
US 2013/0131604 A1    May 23, 2013

Related U.S. Application Data

(60) Provisional application No. 61/327,284, filed on Apr. 23, 2010.

(30) Foreign Application Priority Data

Jul. 29, 2010    (EP) .................................... 10171170

(51) Int. Cl.
| | | |
|---|---|---|
| A61M 5/315 | (2006.01) | |
| A61M 5/24 | (2006.01) | |
| A61B 8/00 | (2006.01) | |
| A61J 1/06 | (2006.01) | |
| A61M 5/14 | (2006.01) | |

(52) U.S. Cl.
CPC ................ *A61M 5/24* (2013.01); *A61B 8/4416* (2013.01); *A61M 5/31536* (2013.01); *A61J 1/062* (2013.01); *A61J 2205/40* (2013.01); *A61M 5/1413* (2013.01); *A61M 5/31551* (2013.01); *A61M 2005/2407* (2013.01); *A61M 2005/2488* (2013.01); *A61M 2205/60* (2013.01); *A61M 2205/6045* (2013.01)

(58) Field of Classification Search
CPC ................. A61M 2205/60; A61M 2205/6045; A61M 2005/2488; A61M 2005/2407; A61M 5/31551; A61M 5/1413; A61M 5/31536; A61M 5/24; A61J 1/062; A61J 2205/40; A61B 8/4416
USPC ......................................... 604/189, 200, 232
See application file for complete search history.

(56) References Cited

U.S. PATENT DOCUMENTS

2009/0259197 A1* 10/2009 Christiansen ................. 604/208
2010/0106099 A1*  4/2010 Christiansen ....... A61M 5/3129
                                                        604/208

FOREIGN PATENT DOCUMENTS

| WO | 2008/009645 | 1/2008 |
| WO | 2008/059063 | 5/2008 |
| WO | WO 2008059063 A1 * | 5/2008 |
| WO | 2008/074897 | 6/2008 |
| WO | WO 2008074897 A1 * | 6/2008 |

OTHER PUBLICATIONS

International Search Report for Int. App. No. PCT/EP2011/056482, completed Oct. 10, 2011.
International Preliminary Report on Patentability for Int. App. No. PCT/EP2011/056482, mailed Nov. 1, 2012.

* cited by examiner

*Primary Examiner* — Theodore Stigell
*Assistant Examiner* — Amber Stiles
(74) *Attorney, Agent, or Firm* — McDonnell Boehnen Hulbert & Berhoff LLP

(57) ABSTRACT

Disclosed herein are cartridge assemblies that include coding features that help dedicate a medicament reservoir to specific injection devices. An exemplary cartridge assembly comprises a cylindrical inner surface for holding medicament and a cylindrical outer surface comprising at its proximal end one or more stops configured as coding elements protruding from the cylindrical outer surface. Each coding element is configured only to engage a corresponding coding feature on a dose setting and delivery mechanism, thereby allowing only the correct cartridge assembly to connect to the dose setting and delivery mechanism.

13 Claims, 10 Drawing Sheets

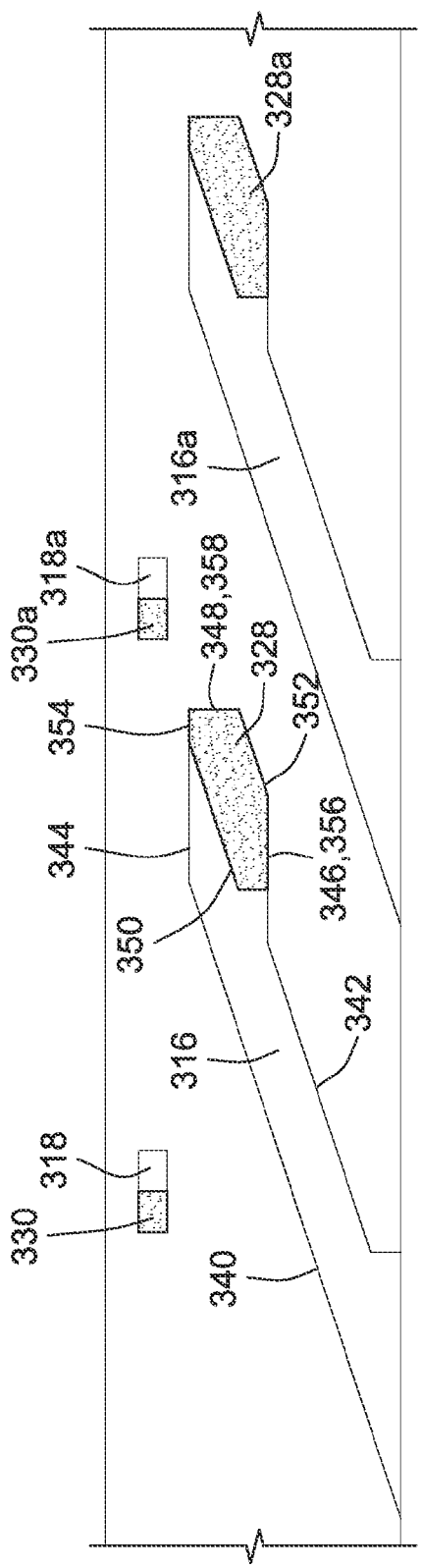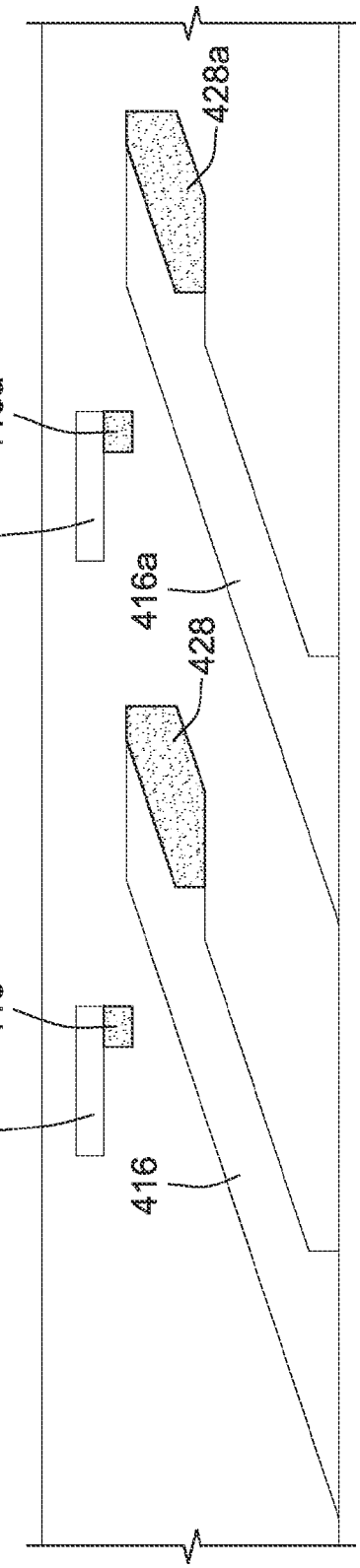

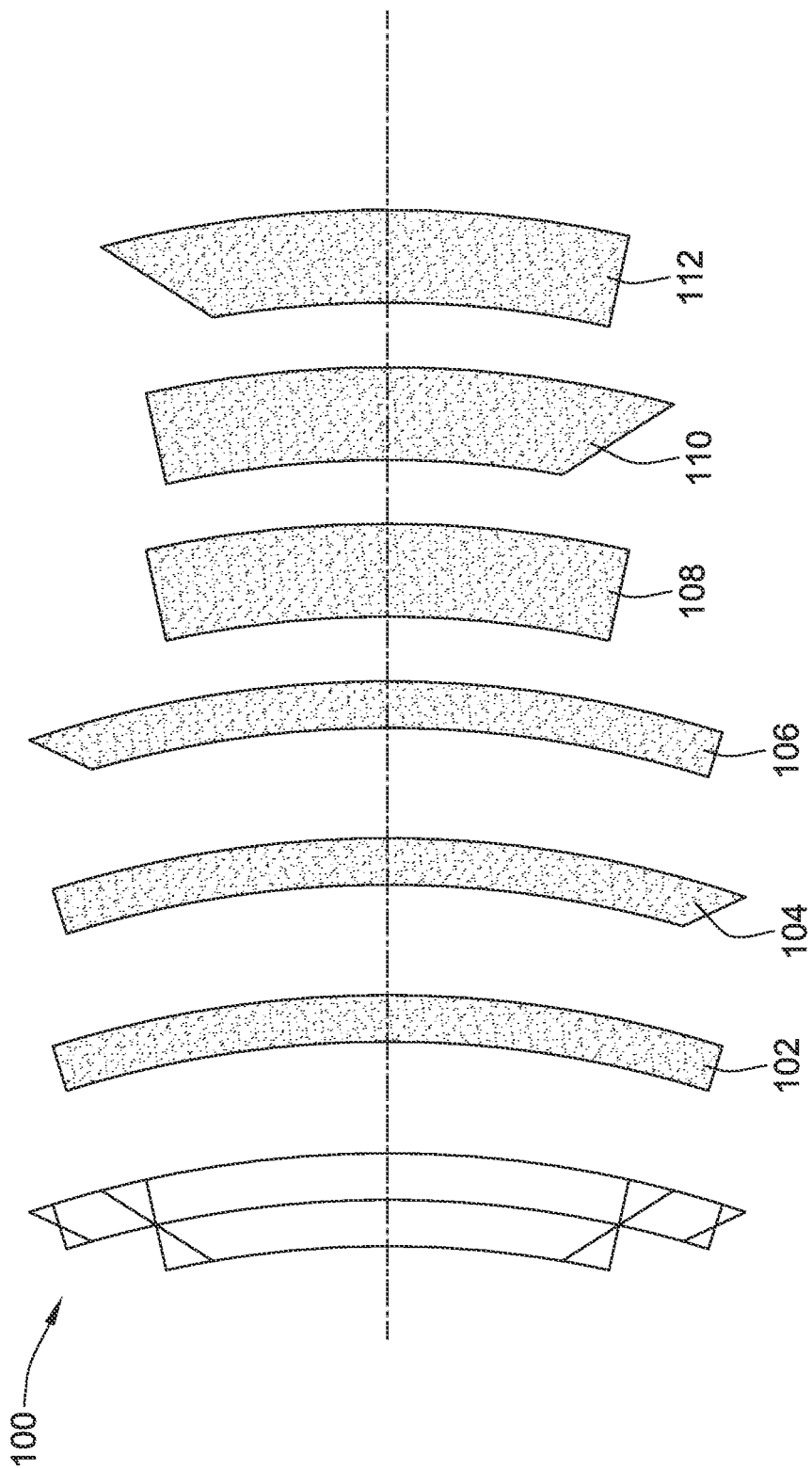

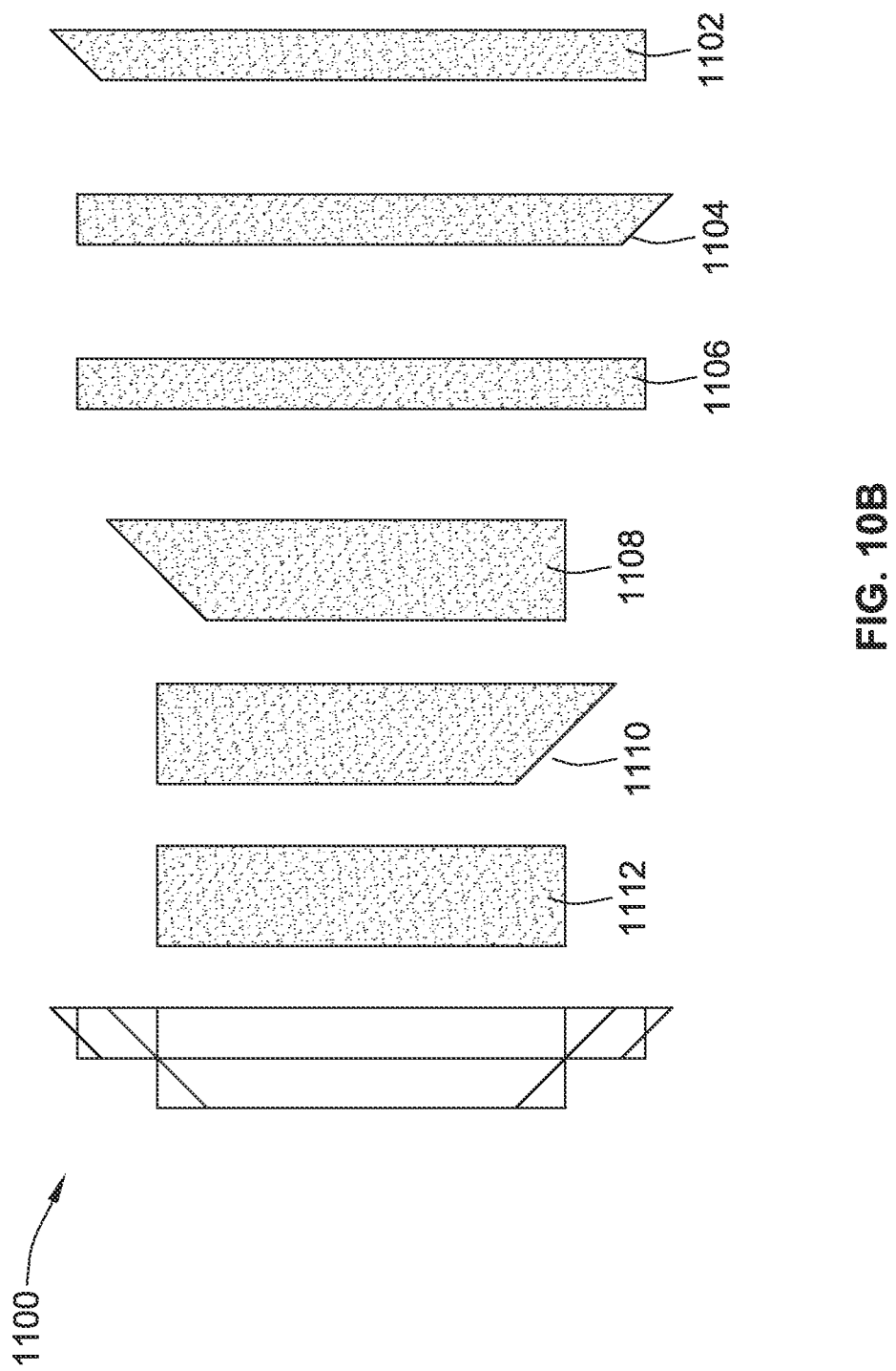

CODED CARTRIDGE ASSEMBLY

CROSS REFERENCE TO RELATED APPLICATIONS

The present application is a U.S. National Phase Application pursuant to 35 U.S.C. §371 of International Application No. PCT/EP2011/056482 filed Apr. 21, 2011, which claims priority to U.S. Provisional Patent Application No. 61/327,284 filed Apr. 23, 2010 and European Patent Application No. 10171170.3 filed Jul. 29, 2010. The entire disclosure contents of these applications are herewith incorporated by reference into the present application.

FIELD OF INVENTION

The present patent application is generally directed to medical delivery devices that comprise a cartridge assembly and a dose setting member, in particular to cartridge assemblies that have coding features, e.g. stop features, that engage complimentary coding features, e.g. counter stop features, on the dose setting member to ensure the appropriate cartridge assembly is connected to the appropriate dose setting member.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a cartridge holder. The cartridge plus the holder is one type of cartridge assembly. After the cartridge has been correctly loaded, the user may then be called upon to select a dose of medicament. Multiple doses may be dosed from the cartridge. Once the cartridge is empty, the cartridge must be removed and replaced with a new cartridge. Most suppliers of such cartridges recommend that the user dispose of the empty cartridges properly.

Such known self-administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, the drug delivery device does not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a correct drug delivery device. However, such color coding schemes pose challenges to certain users, especially those users suffering from poor eyesight or color blindness: a situation that can be quite prevalent in patients suffering from diabetes.

Another concern that may arise with disposable replaceable cartridges is that these cartridges are manufactured in essentially standard sizes and must comply with certain recognized local and international standards. Consequently, such cartridges are typically supplied in standard sized cartridges (e.g., 3 ml cartridges). Therefore, there may be a variety of cartridges supplied by a number of different suppliers and containing different medicament but that may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps not designed or intended for use with such a cartridge and therefore the medicament contained within that cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code the fastening features that allow cartridge assemblies, whether it is a cartridge holder or a molded cartridge without a separate holder, to be attached to dose setting portion of an injection device. In this way a particular drug type or types are linked to the appropriate injection device (e.g., dose setting member). Similarly, there is also a general need for a dedicated cartridge that allows the medical delivery device to be used with only an authorized cartridge containing a specific medicament and preventing undesired cartridge cross-use. There is also a general need to provide a dedicated fastening feature on the cartridge assembly that is difficult to tamper with so that the cartridge assembly may not be compromised in that the medicament can be used with an unauthorized drug or drug delivery device. Because such cartridge assemblies may be difficult to tamper with, they may also reduce the risk of counterfeiting: i.e., making it more difficult for counterfeiters to provide unregulated counterfeit products.

It is an aim to provide an improved coded cartridge assembly to be attached to a dose setting member of an injection device.

SUMMARY

This aim may be achieved by a cartridge assembly which is configured to be connected to a dose setting and delivery mechanism, the cartridge assembly comprising a cylindrical body for holding a medicament reservoir, where the cylindrical body has a proximal end having an outer surface and an inner surface. A fastener is provided on either the outer surface or the inner surface of the proximal end portion, the fastener being suitable for attaching the cartridge assembly to dose setting and delivery mechanism. The cartridge assembly further comprises at least one coding feature that is separate from the fastener. In one embodiment the coding feature is coded to engage a corresponding coding feature on the dose setting and delivery mechanism, thereby allowing the cartridge assembly to operably connect to the dose setting and delivery mechanism. The coding feature ensures that the cartridge assembly can be attached to the corresponding dose setting and delivery mechanism so that the device is operable. If a user tries to attach the cartridge assembly to another dose setting device, the code features would block attachment.

Disclosed herein are cartridge assemblies that include coding features that help dedicate a medicament reservoir to specific injection devices. An exemplary cartridge assembly comprises a cylindrical inner surface for holding medicament and a cylindrical outer surface comprising at its proximal end one or more stops configured as coding elements protruding from the cylindrical outer surface. Each coding element is configured only to engage a corresponding coding feature on a dose setting and delivery mechanism, thereby allowing only the correct cartridge assembly to connect to the dose setting and delivery mechanism.

A injection device may be a drug delivery device designed to dispense a selected dose of a drug, e.g. insulin, insulin analogues, growth hormones, heparins and their derivates etc., optionally suitable for self-administration. The dose may be fixed or variable. The device may be of mechanical type or may comprise electronic elements. The device may be a mobile, hand-held device, e.g. a drug delivery pen type device. The device may be disposable or reusable. The device comprises a dose setting and delivery mechanism, in short dose setting member, which enables to set and deliver a dose.

A cartridge assembly may be formed as a cartridge holder suitable for containing a cartridge or as a molded cartridge without separate holder. The fastener is suitable to connect the cartridge assembly to the dose setting and delivery mechanism. The fastener may be selected from the group consisting of threads, pins and grooves, pins and ridges, bayonet, snap-fit, and detents. A cylindrical body may be a tubular body which may have an essentially circular cross section. The form of the cross section is not limited to a circle.

The coding features may be located on either the outer surface, the inner surface, or an axial end of the cylindrical body. The coding feature may be any indentation or protrusion, in any direction, of any size, and/or of any shape, from a cartridge holder or dose setting member. The coding feature and the corresponding coding feature match so that the cartridge assembly can be operably connected to the dose setting and delivery mechanism, when the coding feature and the corresponding coding feature engage which may mean interlocking of the coding feature and the corresponding coding feature. In other words, if the dose setting and delivery mechanism does not comprise corresponding coding features, the cartridge assembly cannot be attached to the dose setting and delivery mechanism so that they accurately fit together and so that the injection device works. The coding feature may be formed as stop feature and the corresponding coding feature may be formed as counter stop feature. The stop feature and the counter stop feature are suitable to interlock or make contact thereby blocking travel in the connection process and allowing the cartridge assembly to operably connect to the dose setting and delivery mechanism. The movement of the cartridge assembly during attachment may be stopped when the stop feature touches the counter stop feature. This enables to attach the cartridge assembly to the dose setting and delivery mechanism so that the injection device is operable. The stop feature may be configured to contact the counter stop feature in an axial, helical or circumferential direction. In one embodiment the stop feature is configured to contact the counter stop feature in the direction that is normal to the direction of travel of the cartridge assembly at the time of contact.

The cartridge assembly may be coded to a dose setting member using stop features that are located at the proximal end of the cartridge assembly to ensure that a user of an injection device does not mistakenly use the incorrect medicament. In one aspect, a cartridge assembly, defined as a cartridge in a holder or a molded cartridge without a separate holder, for containing a reservoir of medicament is disclosed having a fastener at the proximal end (i.e. the end that attaches to a dose setting device), which includes one or more coding features matched to a fastener located on the distal end of a dose setting device. The fastener/coding features operably connect the cartridge assembly to matched fastener/coding features on the dose setting device, thus allowing the user to administer an injection of the desired medicament.

The integral coding/fastener features can comprise combinations, such as, a pin and ridge, a pin and a pin, a ridge and a pair of pins, a pin and groove, and a screw thread. The use of detents to lock the cartridge assembly to the dose setting member is also advantageous. The cartridge assembly comprises a tubular member having a cylindrical inner surface and a cylindrical outer surface having a fastener on either surface comprising a first coding feature that is coded to engage a second coding feature on a complimentary fastener on a dose setting member, thereby allowing the cartridge assembly to operably connect to the dose setting member. The coding features integral with the cartridge assembly fastener and the complementary fastener on the dose setting assembly can be any combination of pins, ridges, ribs, grooves, slots, protrusions, valleys, and like structures provided that coding features are matched and allow to two assemblies to be operably connected, i.e. like a key in a lock or pieces in a jigsaw puzzle.

In one possible exemplary embodiment, the cartridge assembly for holding a medicament reservoir, the assembly comprises a cylindrical body for holding the medicament reservoir, where the cylindrical body has a proximal outer surface positioned between a shoulder and a proximal axial end that also has a fastener on the proximal outer surface. There is at least one stop on the proximal outer surface that is coded to engage a corresponding coding stop feature on a dose setting member, thereby allowing the assembly to operably connect to the dose setting member. In a preferred configuration the stop is a pin that abuts a proximal facing surface of the shoulder which may be positioned on the outer surface of the proximal end. This stop can be a radial pin or an axial pin. Likewise, there can be a plurality of stops offset from each other and/or different in size in the axial, circumferential or radial extent from each other. Most preferably, the stop is separate from the fastener.

In yet another configuration the stop is an indentation and the corresponding coding stop feature located on the dose setting member is a pin.

In one embodiment the cartridge assembly is configured to be rotated until the pin contacts a counter stop face of a groove feature that is an axial indentation on a circular ridge of dose setting mechanism.

A medicament delivery device may comprise a dose setting member and a cartridge assembly for holding a medicament reservoir, where the assembly comprises a cylindrical body for holding the medicament reservoir, where the cylindrical body has a proximal outer surface positioned between a shoulder and a proximal axial end. There is a fastener on the proximal outer surface having a connecting direction and at least one stop on the proximal outer surface that is coded to engage a corresponding coding feature on the dose setting member, wherein the dose member allows the assembly to operably connect to the dose setting member.

The corresponding coding feature on the dose setting member is a counter stop and the engagement is on a face that lies in the radial plane of the counter stop. Alternatively, the corresponding coding feature on the dose setting member is a counter stop and the engagement with the stop is on a face that lies in the longitudinal plane. The direction of contact between the corresponding stop features would preferably be normal to the fastener connecting direction. Further, the corresponding coding feature could be an indentation configured to accept the stop when the dose setting member and cartridge assembly are operably connected.

Coding may be achieved by varying the coding features in a number of ways including, but not limited to, the following:
  i. Number of features.
  ii. Position of features—axial/circumferential/radial, especially relative to a standard feature, e.g. axial length from one end or from a fastening means.
  iii. Size of features, e.g. axial/circumferential/radial extent. The size of each feature may be different from at least one of the others, e.g. a number of coding pins with different radial extents.
  iv. Cross-sectional shape of the features in any plane, e.g. longitudinal, transverse, or normal to a helix, but preferably in a plane normal to the fastening action.

The angle of coding faces on the cartridge assembly and the complimentary coding feature on the dose setting member and the way that they contact each other may be in any direction. For example, contact may be in the axial/helical/circumferential directions, although preferably in the direction of the fastening action. The coding features may be pins or cover a significant proportion of the outside of the cartridge assembly.

If the cartridge assembly fits in only one orientation, the number of coding combinations is increased. This might be achieved if one or more of the coding features (or an additional feature) has an asymmetric position or size around the axis, or if one of the features is unique, e.g. an indentation that is smaller than all the others. Alternatively, the coding may be included more than once, offering redundancy in case one set of coding is damaged, and also allowing the user to insert the cartridge assembly in more than one orientation.

Coding may depend on more than one coding feature. A coding system may consist of a number of features, one of which blocks travel earlier in the fastening action than all other features, and one of which blocks travel later than all other features. With only one feature, a coding feature that blocks travel early in the fastening action will fit into a device where travel should be blocked later. By combining two features, all drugs can be prevented from fitting into the wrong devices.

In one embodiment a first and a second cartridge assembly are provided where the first cartridge assembly holds a first medicament and the second cartridge assembly holds a second medicament different from the first medicament. The coding feature of the first cartridge assembly is unique to the first medicament and is specifically coded to engage only a corresponding coding feature on a dose setting and delivery mechanism that is configured to dispense the first medicament and where the second cartridge assembly will not operably connect to the first dose setting and delivery mechanism.

The coding feature of the second cartridge assembly may be unique to the second medicament and is specifically coded to engage only a corresponding coding feature on a dose setting and delivery mechanism that is configured to dispense the second medicament.

A third cartridge assembly holding a third medicament different from the first and second medicaments may be provided, where the coding feature of the third cartridge assembly is unique to the third medicament and where the third cartridge assembly operably connects only to a third dose setting and delivery mechanism that is different from other dose setting and delivery mechanisms. The first and second cartridge assemblies are a collection of cartridge device, where the coding features prevents that the cartridge assemblies are attached to the wrong dose setting and delivery mechanisms.

In one embodiment the cartridge assemblies have the same type of fasteners, and wherein the coding feature of the first assembly is different from the coding feature of the second assembly. Thus, the handlings of the cartridge assemblies are similar, but none of the cartridge assemblies in the system can be fitted to incorrect devices.

A collection of cartridge assemblies each having coded stop features to allow for connection of reservoirs of different medicaments to specific matched dose setting members to make up a family of injection devices. For example, the collection can have two or more cartridge assemblies, where a first cartridge assembly comprises (a) a tubular member having a cylindrical inner surface and a cylindrical outer surface at a proximal end, (b) a first medicament inside the tubular member, (c) a fastener on the cylindrical outer or inner surface of the tubular member, and (d) a coded stop separate from the fastener located on the proximal end of the tubular member comprising a first coding feature that is unique to the first medicament and is specifically coded to engage only a corresponding coding stop feature on a dose setting member on a first dose setting member that is configured to dispense the first medicament. The first coding feature is different than a second coding feature on a coded stop on a second cartridge assembly in the collection that contains a second medicament, where the first and second medicaments are different and where the second cartridge assembly will not operably connect to the first dose setting member, thereby preventing the first dosing setting member from administering the second medicament.

Additionally, the collection could further comprise a third cartridge assembly having a coded stop comprising a third coding feature unique to a third medicament contained in the third cartridge assembly that is different than the first and second medicaments and where the third cartridge assembly operably connects only to a third dose setting member that is different from other dose setting members in the family of injection devices. All the coded stops of the cartridge assemblies in the collection may also have the same type of fastening feature selected from the group consisting of threads, pins & grooves, pins & ridges, bayonet, snap-fit, and detents, and wherein each coding feature associated with each coded stop is different from all the other coding features on the other coded stops on the cartridge assemblies in the collection.

In a system in which helical travel is followed by rotational travel, coding features may prevent travel into the rotational phase if the drug is incorrect. This will make it obvious to the user that the drug is incorrect. The fastening action may stop due to features within the fastening means, e.g. when the pin reaches the end of the groove. Alternatively, the coding features may provide the only stop. If the coding features provide the stop, the cartridge assembly may over-rotate if the incorrect drug is inserted. It may then be ejected along a groove, which may have a one-way element to prevent entry into the groove during normal fastening. Although preferred embodiments are illustrated with the fastening means as a pin on the device following a groove on the cartridge assembly, and the travel is axial then helical then rotational, the coding may be used with any fastening means and any combination of directions in the travel, including purely axial travel.

Coding could block all incorrect drugs or just the most dangerous, e.g. a short-acting drug can be fitted into a device intended for long-acting drugs, or a low concentration drug into a device for high concentration, but not vice versa. Coding features may be detected by electro-mechanical means, e.g. microswitches, or optical/magnetic switches. A programmable pen could then respond to the drug type, e.g. by limiting the maximum dose.

These as well as other advantages of various aspects will become apparent to those of ordinary skill in the art by reading the following detailed description, with appropriate reference to the accompanying drawings.

The terms "drug" or "medicament", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36[Asp28] Exendin-4(1-39),
des Pro36[IsoAsp28] Exendin-4(1-39),
des Pro36[Met(O)14, Asp28] Exendin-4(1-39),
des Pro36[Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36[Met(O)14 Trp(O2)25, Asp28] Exendin-4(1-39),
des Pro36[Met(O)14 Trp(O2)25, IsoAsp28] Exendin-4(1-39); or
des Pro36[Asp28] Exendin-4(1-39),
des Pro36[IsoAsp28] Exendin-4(1-39),
des Pro36[Met(O)14, Asp28] Exendin-4(1-39),
des Pro36[Met(O)14, IsoAsp28] Exendin-4(1-39),
des Pro36[Trp(O2)25, Asp28] Exendin-4(1-39),
des Pro36[Trp(O2)25, IsoAsp28] Exendin-4(1-39),
des Pro36[Met(O)14 Trp(O2)25, Asp28] Exendin-4(1-39),
des Pro36[Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)$_6$-des Pro36[Asp28] Exendin-4(1-39)-Lys6-NH2,
Des Asp28 Pro36, Pro37, Pro38Exendin-4(1-39)-NH2,
H-(Lys)$_6$-des Pro36, Pro38[Asp28] Exendin-4(1-39)-NH2,
H-Asn-(Glu)$_5$des Pro36, Pro37, Pro38[Asp28] Exendin-4(1-39)-NH2,
des Pro36, Pro37, Pro38[Asp28] Exendin-4(1-39)-(Lys)$_6$-NH2,
H-(Lys)$_6$-des Pro36, Pro37, Pro38[Asp28] Exendin-4(1-39)-(Lys)$_6$-NH2,
H-Asn-(Glu)$_5$-des Pro36, Pro37, Pro38[Asp28] Exendin-4(1-39)-(Lys)$_6$-NH2,
H-(Lys)$_6$-des Pro36[Trp(O2)25, Asp28] Exendin-4(1-39)-Lys6-NH2,
H-des Asp28 Pro36, Pro37, Pro38[Trp(O2)25] Exendin-4(1-39)-NH2,
H-(Lys)$_6$-des Pro36, Pro37, Pro38[Trp(O2)25, Asp28] Exendin-4(1-39)-NH2,
H-Asn-(Glu)$_5$-des Pro36, Pro37, Pro38[Trp(O2)25, Asp28] Exendin-4(1-39)-NH2,
des Pro36, Pro37, Pro38[Trp(O2)25, Asp28] Exendin-4(1-39)-(Lys)$_6$-NH2,
H-(Lys)$_6$-des Pro36, Pro37, Pro38[Trp(O2)25, Asp28] Exendin-4(1-39)-(Lys)$_6$-NH2,
H-Asn-(Glu)$_5$-des Pro36, Pro37, Pro38[Trp(O2)25, Asp28] Exendin-4(1-39)-(Lys)$_6$-NH2,
H-(Lys)$_6$-des Pro36[Met(O)14, Asp28] Exendin-4(1-39)-Lys6-NH2,
des Met(O)14 Asp28 Pro36, Pro37, Pro38 Exendin-4(1-39)-NH2,
H-(Lys)$_6$-des Pro36, Pro37, Pro38[Met(O)14, Asp28] Exendin-4(1-39)-NH2,
H-Asn-(Glu)$_5$-des Pro36, Pro37, Pro38[Met(O)14, Asp28] Exendin-4(1-39)-NH2,
des Pro36, Pro37, Pro38[Met(O)14, Asp28] Exendin-4(1-39)-(Lys)$_6$-NH2,
H-(Lys)$_6$-des Pro36, Pro37, Pro38[Met(O)14, Asp28] Exendin-4(1-39)-(Lys)$_6$-NH2,
H-Asn-(Glu)$_5$ des Pro36, Pro37, Pro38[Met(O)14, Asp28] Exendin-4(1-39)-(Lys)$_6$-NH2,
H-Lys6-des Pro36[Met(O)14, Trp(O2)25, Asp28] Exendin-4(1-39)-Lys6-NH2,
H-des Asp28 Pro36, Pro37, Pro38[Met(O)14, Trp(O2)25] Exendin-4(1-39)-NH2,
H-(Lys)$_6$-des Pro36, Pro37, Pro38[Met(O)14, Asp28] Exendin-4(1-39)-NH2,
H-Asn-(Glu)$_5$-des Pro36, Pro37, Pro38[Met(O)14, Trp(O2)25, Asp28] Exendin-4(1-39)-NH2, des Pro36, Pro37, Pro38[Met(O)14, Trp(O2)25, Asp28] Exendin-4(1-39)-(Lys)$_6$-NH2, H-(Lys)$_6$-des Pro36, Pro37, Pro38[Met(O)14, Trp(O2)25, Asp28] Exendin-4(S1-39)-(Lys)$_6$-NH2, H-Asn-(Glu)$_5$-des Pro36, Pro37, Pro38[Met(O)14, Trp(O2) 25, Asp28] Exendin-4(1-39)-(Lys)$_6$-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na$^+$, or K$^+$, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 4A shows the interaction of exemplary coding features on a cartridge holder with exemplary coding features on a dose setting member;

FIG. 4B also shows the interaction of exemplary coding features on a cartridge holder with exemplary coding features on a dose setting member;

FIG. 10A shows exemplary cross-sections of the coding features; and

FIG. 10B shows exemplary cross-sections of the coding features from a different perspective than shown in FIG. 10A.

DETAILED DESCRIPTION

Figure 1:
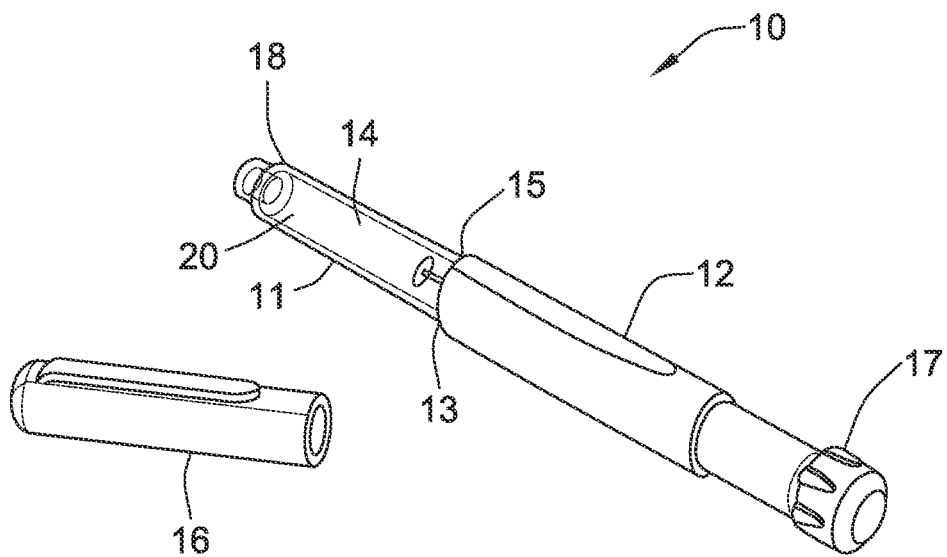
FIG. 1 illustrates a pen type drug delivery device.

Referring to FIG. 1, there is shown a drug delivery device 10 in the form of a pen type syringe. This drug delivery device 10 comprises a dose setting member 12 which serves as dose setting and delivery mechanism, a cartridge holder 14, and a removable cap 16. A proximal end 15 of the cartridge holder 14 and a distal end 13 of the dose setting member 12 are removably secured together. The pen type syringe may comprise a re-usable or a disposable pen type syringe. Where the syringe comprises a re-usable device, the cartridge holder 14 and the dose setting mechanism are removably coupled together. In a disposable device, they may be permanently coupled together. When the drug delivery device is not in use, the removable cap 16 can be releasably retained over the cartridge holder 14.

Figure 2:
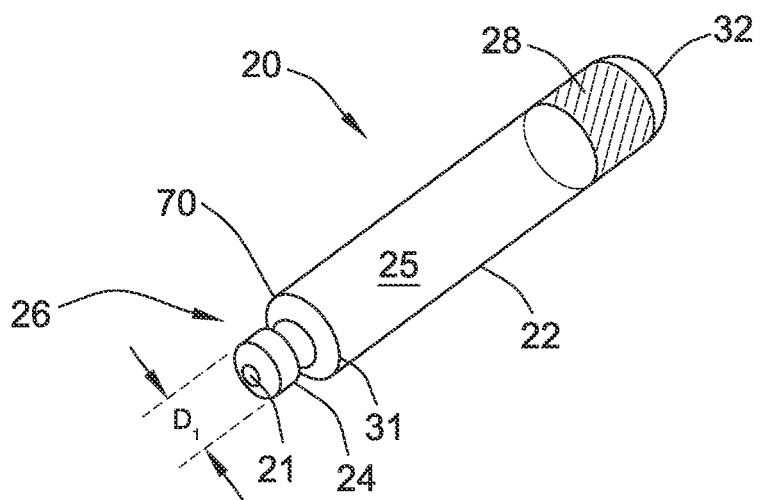
FIG. 2 illustrates a cartridge that may be loaded into a cartridge holder of the pen type drug delivery device illustrated in FIG. 1.

The cartridge holder contains a removable cartridge 20 containing a medicament 25. Referring to FIG. 1, the cartridge holder 14 houses a removable cartridge 20. FIG. 2 illustrates a perspective view of the cartridge 20 that may be used with the drug delivery device illustrated in FIG. 1.

An inner cartridge cavity 11 defined by the cartridge holder 14 is dimensioned and configured to securely receive and retain the cartridge 20. The cartridge 20 includes a generally tubular barrel 22 extending from a distal end 31 to a proximal end 32. The distal end 31 is defined by an inwardly converging shoulder 70.

At the distal end 31, the cartridge 20 includes a smaller diameter neck 26, and this neck 26 projects distally from the shoulder 70 of the barrel 22. Preferably, this smaller diameter neck 26 is provided with a large diameter annular bead (not shown) and this bead extends circumferentially thereabout at the extreme distal end of the neck 26. A pierceable seal or septum 21 is securely mounted across the open distal end defined by the neck. The seal 21 may be held in place by a metallic sleeve 24. This sleeve 24 may be crimped around the circumferential bead at the distal end of the neck 26. The medicament is pre-filled into the cartridge 20 and is retained within the cartridge, in part, by the pierceable seal 21, the metallic sleeve 24, and the stopper 28. The stopper 28 is in sliding fluid-tight engagement with the inner tubular wall of the barrel 22. Forces directed axially in the distal direction upon the stopper 28 during dose administration urges the medication from the cartridge 20 though a double ended needle mounted onto the distal end of the cartridge holder 14.

A number of doses of a medicament may be dispensed from the cartridge 20. Preferably, the cartridge 20 contains a type of medicament that must be administered often, such as once or more times a day. One such medicament is insulin. A movable piston which also serves as stopper 28 is retained in a first end or proximal end of the cartridge 20.

A portion of the cartridge holder 14 defining the cartridge holder cavity 11, which is formed by the inner cylindrical wall of cartridge holder 14, is of substantially uniform diameter and is smaller than the cartridge diameter of cartridge 20 represented in FIG. 2 by $D_1$. The interior of the cartridge holder 14 includes an inwardly-extending annular portion or stop 18 that is dimensioned to prevent the cartridge 20 from moving within the cartridge holder 14. In this manner, when the cartridge 20 is loaded into the cavity 11 of the cartridge holder 14 and the cartridge holder 14 is then connected to the dose setting member 12, the cartridge 20 will be securely held within the cartridge cavity 11.

The dose setting member 12 comprises a dose setter 17 at the proximal end of the dose setting member 12. In one preferred arrangement, the dose setter 17 is rotated to set a dose. To administer this set dose, the user attaches the needle assembly (not shown) comprising a double ended needle on the distal end of the cartridge holder 14. In this manner, the needle assembly pierces the seal 21 of the cartridge 20 and is therefore in liquid communication with the medicament. The user pushes on the dose setter 17 to inject the set dose. The same dose setting and dose administration procedure is followed until the medicament in the cartridge 20 is expended and then a new cartridge must be loaded in the device 10. To exchange an empty cartridge 20, the user is called upon to remove the cartridge holder 14 from the dose setting member 12.

In general, cartridge dedication (e.g., the coding of a particular cartridge holder to a matching dose setting member) may be achieved by arranging coding features on the cartridge holder 14 to align with coding features on the corresponding dose setting member 12 so as to require an identifiable connection path (e.g., a distinct sequence of axial, helical, and/or rotational movements) and/or prevent mismatched cartridge holders 14 and dose setting members 12 from being connected. Typically, the coding features align so that rotation in one direction (i.e., clockwise or counterclockwise) causes the shoulder of the cartridge holder 14 and the distal end 13 of the dose setting member to move towards each other, or in other words, connects the cartridge holder 14 and the dose setting member 12. Rotation in the opposite direction may therefore disconnect the cartridge holder 14 and the dose setting member 12 (e.g., cause the shoulder of the cartridge holder 14 and the distal end 13 of the dose setting member 12 to move away from each other).

Figure 3:
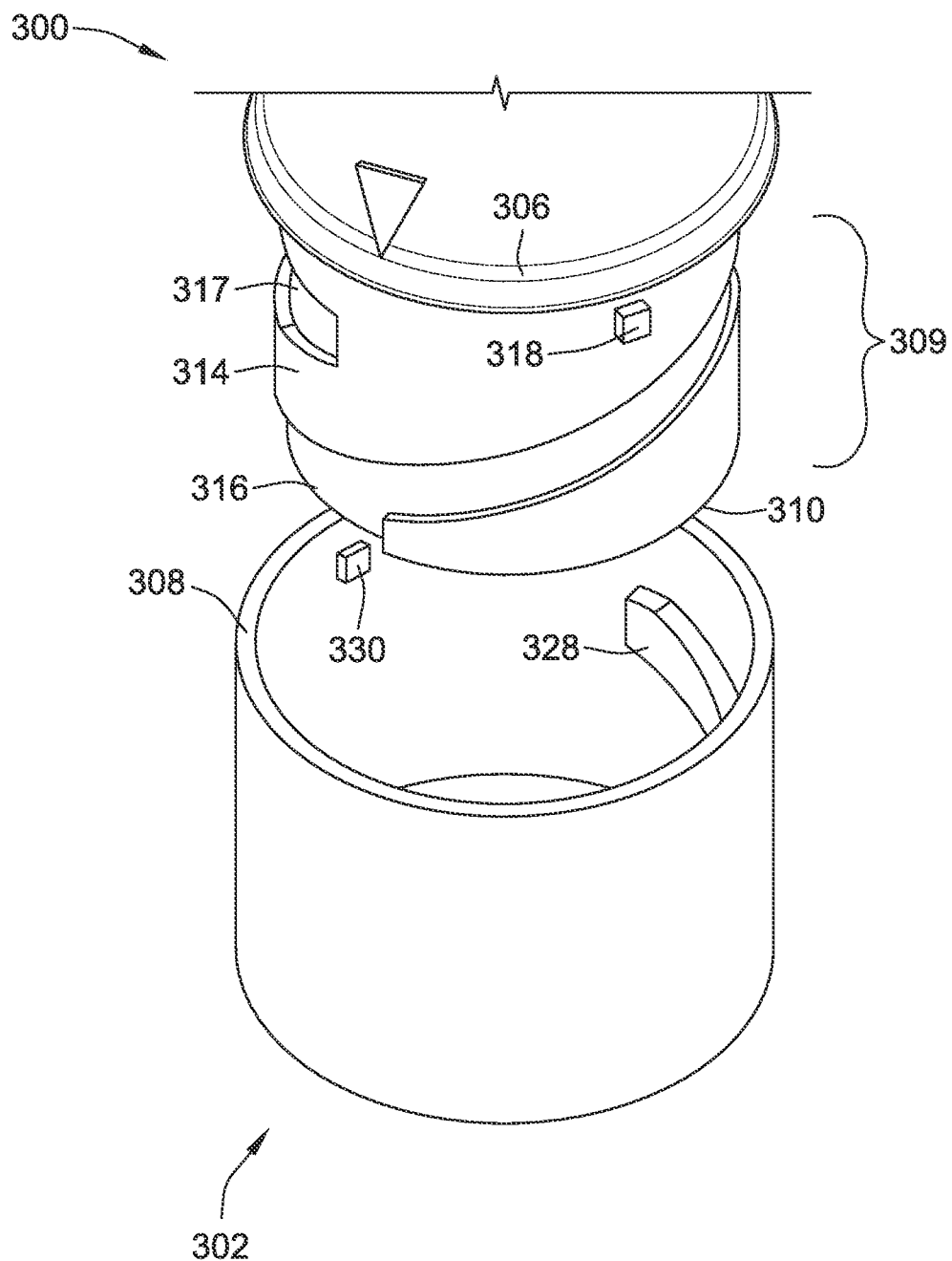
FIG. 3 illustrates an arrangement of a cartridge holder that includes coding features that help dedicate the cartridge holder to a particular dose setting member.

FIG. 3 illustrates a first arrangement of a cartridge holder 300 that includes coding features that help dedicate the cartridge holder 300 to a particular dose setting member 302. The cartridge holder 300 has a tubular body having a cylindrical inner surface that defines the cavity designed to hold a medicament cartridge. Cartridge holder 300 and connector portion 309 defines a cylindrical inner wall and a cylindrical outer wall 314. The tubular body extends from the stop (not shown) to a shoulder 306. Shoulder 306 is arranged such that when cartridge holder 300 is connected to dose setting member 302, the proximal side of shoulder 306 sits flush against the distal end 308 of the dose setting member 302. A connector portion 309 of cartridge holder 300 extends from the shoulder 306 to a proximal end 310 of cartridge holder 300. Fastening groove 316 on the connector portion 309 engages fastening pin 328 on the inside surface of dose setting member 302 to form the fastening means to connect the cartridge assembly to the dose setting member 302. The fastening pin 328 may move along to the groove 316 to its end portion 317. Likewise, it should be understood that embodiments with a single groove feature or more than two groove features, as well as embodiments with differently shaped groove features, are also possible. Alternatively, the fastening groove 316 could be located on the dose setting member 302 and the fastening pin 328 could be located on the cartridge assembly. Indeed, generally, any fastener feature known to art of injection devices may be used.

Also included on the connector portion 309 is a coding feature, illustrated as a stop 318. This coding feature has a complimentary coding feature on dose setting member 302, shown as a counter stop 330. More generally, a coding feature may be any indentation or protrusion, in any direction, of any size, and/or of any shape, from a cartridge holder 300 or dose setting member 302. As illustrated, the coding feature 318 is a square-shaped protrusion, however, such stop features may vary in size, shape, and location. For instance, a coding feature may be defined by helical, rotational, and/or axial surfaces of varying number and extent. Preferably, these coding features on cartridge holder 300 and dose setting member 302 are coded such that, if the particular cartridge holder is not intended for the particular dose setting member, the coding features will prevent proper connection, or otherwise indicate that cartridge holder 300 and dose setting member 302 are mismatched.

FIGS. 4 to 6 show in greater detail the interaction between coding features on the cartridge holder 300 and dose setting member 302, illustrated as projections around the circumference. Shaded features are on one part and plain features are on the other, for example if shaded features are on the dose setting member 302 then the plain features would be on the cartridge holder 300. In particular, FIG. 4A shows the interaction of coding features 316 and 318, and fastener 328, 328*a*, 330, and 330*a*. Note that a second set of coding features 316*a* and 318*a*, which may be identical to coding features 316 and 318 are also illustrated. The various coding features on the dose setting member 302 may work together to help dedicate a particular cartridge holder 300 to particular dose setting member 302. For example, FIGS. 4A and 4B show how the coding features of cartridge holder 300 preferably align with the coding features of the dose setting member 302 when properly connected. In particular, when properly connected stop feature 318 securely engages counter stop 330.

More specifically, fastening groove feature 316 and fastening pin feature 328 are configured such that cartridge holder 300 and dose setting member 302 may be connected by guiding the dose setting member axially, helically, and then rotationally, until axial surface 348 of the cartridge holder 300 contacts the axial surface 358 of dose setting member 302. A proximal surface 346 of the cartridge holder 300 contacts a distal surface 356 of the dose setting member 302. This arrangement thus helps code cartridge holder 300 to dose setting member 302. And, if fastening pin feature 328 is not coded to match fastening groove feature 316, then the pin feature will either be blocked (e.g., the pin feature has an axial extent greater than the axial extent of the groove feature between the proximal and distal helical surfaces 340, 342), or will not fit securely (e.g., the pin feature has an axial extent less than the axial extent of the groove feature between the proximal and distal helical surfaces 340, 342). Although the main coding is between 330 and 318, the coding could also be fastening pin to groove. Additionally, if coding feature 330 is not coded to match coding feature 318, then coding feature 318 may contact coding feature 330 too early and hence prevent complete assembly of fastening pin 328 into fastening groove feature 342.

FIG. 4B shows an alternative embodiment also comprising fastening groove features 416, 416a and fastening pin features 428, 428a where coding features 418, 418a are counter stops located on the dose setting member and coded to engage stops 430, 430a by making contact along at least the axial face. However, contact between the stop features may be in any direction such as axial, helical or circumferential, although the direction of contact would preferably be normal to the direction of travel at the time of contact. For example in other embodiments, such as those shown in FIGS. 5A, 5B and 5C, coding features having a longitudinal portion 510a-c and radial portions 512a-c, block both rotational and axial movement.

Figure 5A:
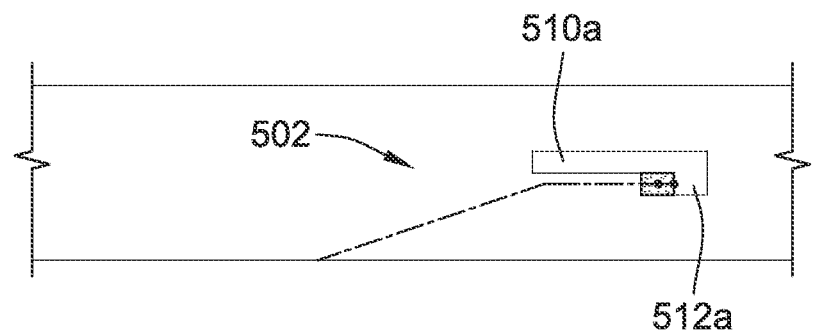
FIG. 5A shows a coding path associated with an exemplary arrangement of coding features.
Figure 5B:
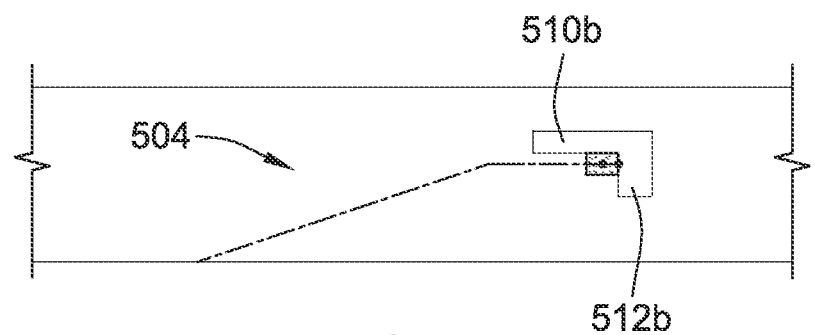
FIG. 5B shows another coding path associated with an exemplary arrangement of coding features.
Figure 5C:
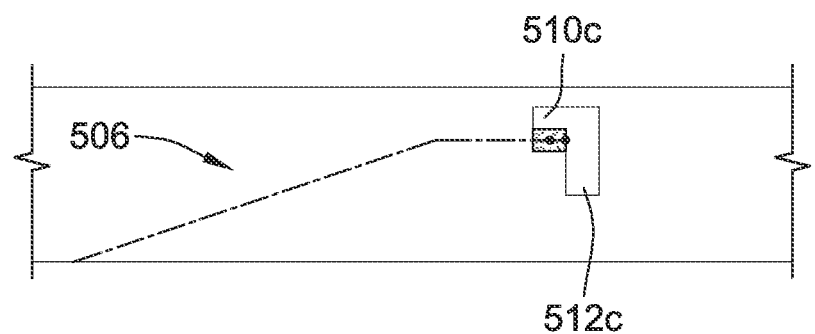
FIG. 5C shows another coding path associated with an exemplary arrangement of coding features.

In preferred embodiments the fastening means would follow the same path for all drugs in the coding system, but the coded blocking or stop features would be offset from the fastening means by a different amount for each drug. As such, coding may be accomplished, at least in part, by varying the axial, radial, and/or circumferential position of the coding features so as to vary the axial, radial, and/or circumferential position of the coding path. The pin and groove of the fastening assembly are not shown, but assembly of the pin into the groove guides the coding features along the coding paths illustrated as dotted lines. The shape of the coding path is therefore defined by the fastening action, for example fastening pin 328 following fastening groove feature 316, but its position passes through the coding features. For instance, FIGS. 5A-C show three different possible coding paths 502, 504, and 506, which may be achieved using various coding-feature configurations. As such, each coding path may be used to dedicate a cartridge holder for a particular medicament to its corresponding dose setting member.

If there is only one coded stop feature, then a cartridge holder where the travel of the stop feature is blocked early in the fastening action will fit into a device where the travel is blocked later. The same problem exists with more than one stop feature, if the all stop features for a given drug are offset by the same distance relative to another drug. FIGS. 5A-C show a coding system that depends on more than one blocking or stopping face, so that all drugs can be prevented from being fitted into an incorrect device. FIG. 5B shows both features in their central position. For the other drugs, i.e. FIGS. 5A and 5C, one coding feature is moved towards the start of the fastening travel, and one coding feature is moved later in the fastening travel. In this way, none of the cartridge assemblies in the system can be fitted to incorrect devices.

Figure 6A:
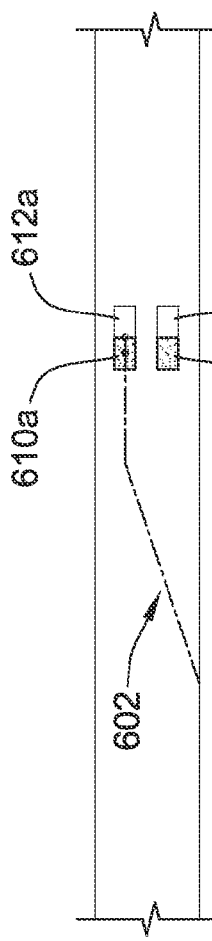
FIG. 6A shows an exemplary arrangement of pin features on a cartridge holder.
Figure 6B:
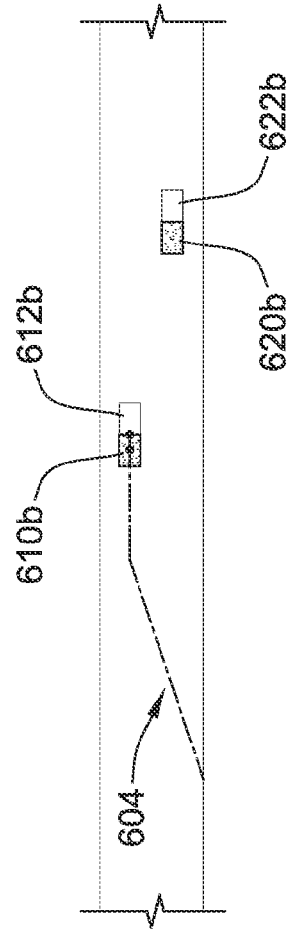
FIG. 6B shows another exemplary arrangement of pin features on a cartridge holder.
Figure 6C:
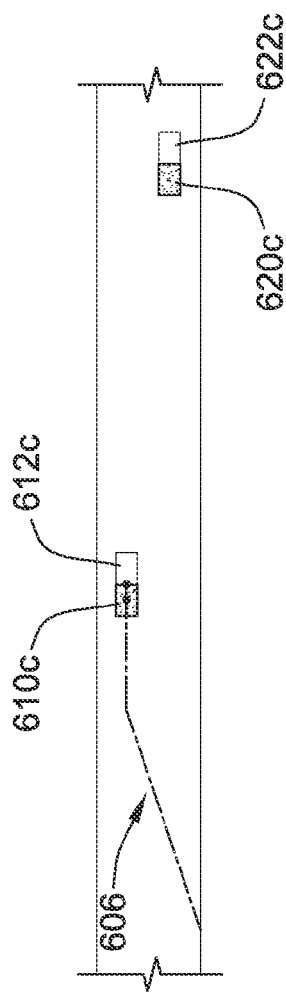
FIG. 6C shows another exemplary arrangement of pin features on a cartridge holder.

FIGS. 6A-C also illustrate exemplary cartridge holders having multiple blocking or stopping faces, which match corresponding coding features on the corresponding dose setting members. In particular, when a user moves coding features 610a and 620a through coding path 602, coding features 610a and 620a of the dose setting member engage features 612a and 622a of the cartridge holder, indicating to the user that the proper connection has been achieved. Similarly, features 610b and 620b may be moved through coding path 604 to engage features 612b and 622b, and features 610c and 620c may be moved through coding path 606 to engage features 612c and 622c.

Since the pairs of features 610a/620a, 610b/620b, and 610c/620c (and their corresponding or complimentary features 612a/622a, 612b/622b, and 612c/622c on the dose setting members), are each oriented differently with respect to each other, one pair may block travel earlier or later in the connection process than another pair, thus helping dedicate a particular cartridge to its corresponding dose setting member. FIG. 6A shows both features in their central position. For the other drugs, i.e., FIGS. 6B and 6C, one coding feature is moved towards the start of the fastening travel, and one coding feature is moved later in the fastening travel. In this way, none of the cartridge assemblies in the system can be fitted to incorrect devices.

Figure 7:
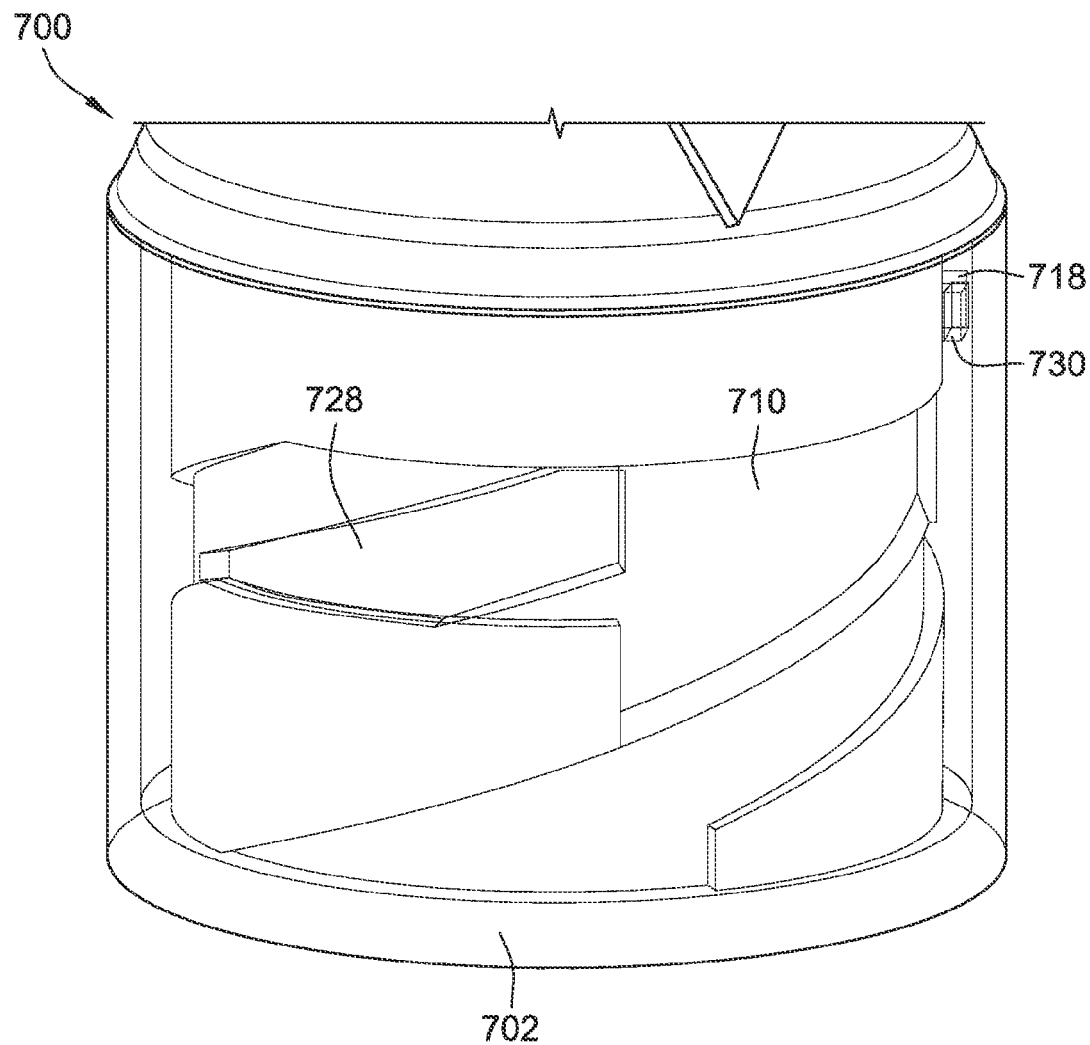
FIG. 7 shows an exemplary cartridge holder having an ejection feature.

In another aspect, a cartridge holder may include an ejection feature, which ejects the cartridge holder if it is inserted into the incorrect dose setting member. FIG. 7 shows an exemplary cartridge holder 700 having an ejection feature. In particular, the fastening groove feature in cartridge holder 700 may include an ejection channel 710. As shown, the coding features are arranged to provide coded stop features 718 and 730 that are arranged to engage and block rotational movement when properly connected. These stops prevent rotational movement of fastening pin feature 728 of the dose setting member 702 into the ejection channel 710. However, if the cartridge holder 700 is inserted into a dose setting member 702 that does not match, i.e. stops 718 and 730 do not engage, then the fastening pin feature 728 on the dose setting member 702 may over-rotate into the ejection channel 710. Once in this channel, the pin 728 will be loose and it will be obvious to the user that the fastening operation has failed. As an added safety measure, the cartridge assembly 700 or the dose setting member 702 can be designed such that further rotation in the fastening direction will force the pin across or into a one-way element. In particular, once in this one-way element the fastening pin contacts a ramp, and the holder (or device) flexes to allow the pin to pass into the start of one of the fastening grooves. The side of the one-way element adjacent to the groove has a steeper angle, so the pin cannot return, or enter the ejection channel during normal fastening. Additionally, a spring mechanism can be added to the device to force the cartridge holder in a distal direction, thus ejecting it from the dose setting member helping to ensure that only a correct cartridge holder is connected.

Figure 8:
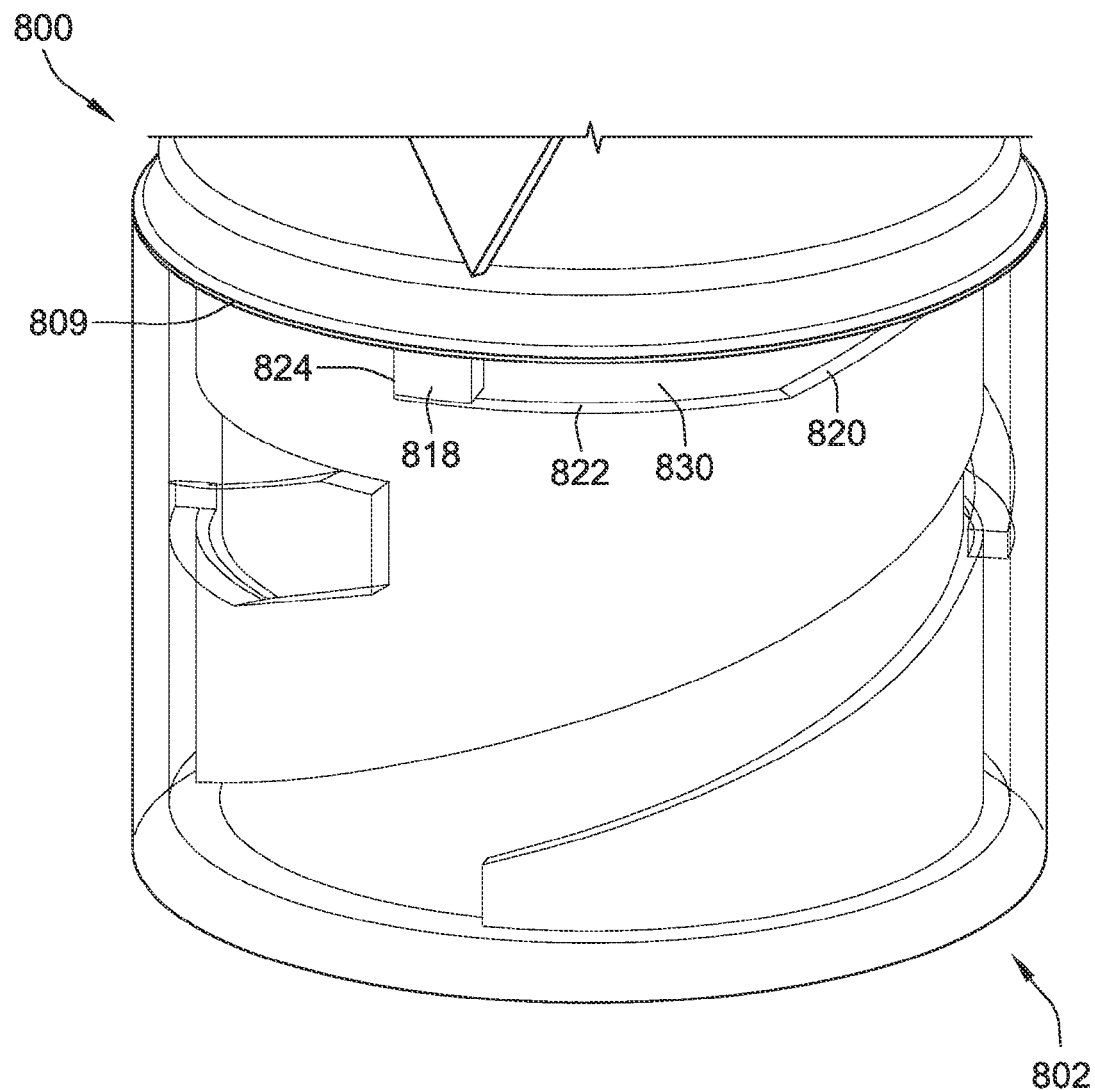
FIG. 8 shows an exemplary cartridge holder having a pin feature extending proximally from the shoulder of the cartridge holder.

FIG. 8 shows an alternative embodiment, which includes a stop feature 818 extending proximally from the shoulder 809 of the cartridge holder 800. Stop feature 818 is coded to match a coded groove feature 830 on dose setting member 802. Specifically, to correctly connect cartridge holder 800 to dose setting member 802, stop feature 818 is moved helically along helical surface 820 until the proximal edge of stop feature 818 contacts the surface 822 of groove feature 830. The cartridge holder 800 is then rotated until the stop feature contacts the axial surface or face of counter stop 824 of groove feature 830, thus stopping rotational movement. This arrangement may be more compact than other embodiments, and the shoulder may help protect the coding features 818, 830 from damage.

Figure 9:
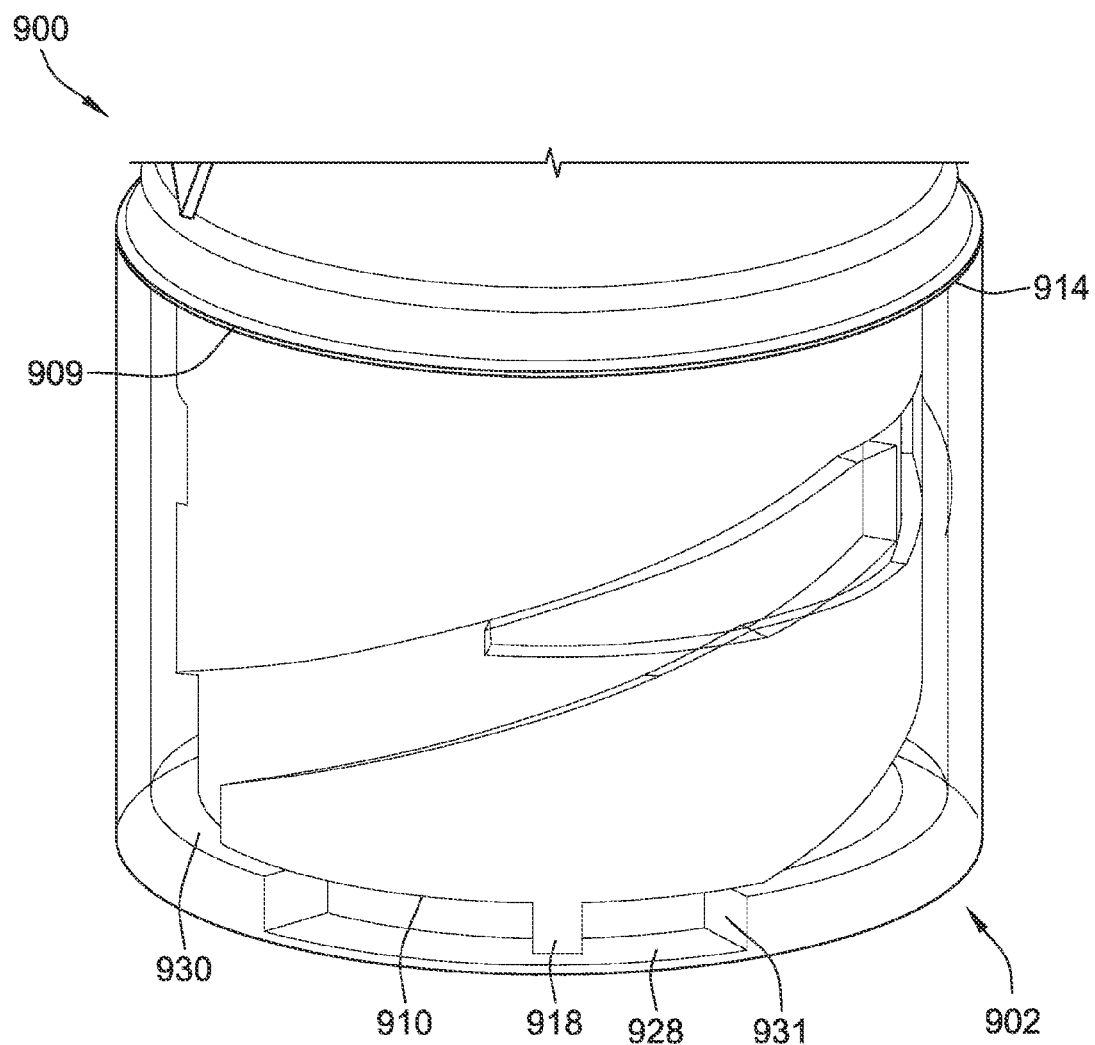
FIG. 9 shows an exemplary cartridge holder having a pin feature extending proximally from the proximal end of the cartridge holder.

FIG. 9 shows another alternative embodiment, which includes a stop feature 918 extending proximally from the proximal end 910 of the cartridge holder 900. Unlike the other stop features discussed herein, this coding feature 918 does not protrude radially from the outer wall of the cartridge holder, but instead protrudes proximally from the proximal end 910 of cartridge holder. The coding feature corresponding to stop feature 918 on dose setting mechanism 902 is coded groove feature 928 with counter stop face 931. Groove feature 928 is an axial indentation on a circular ridge 930 of dose setting mechanism 902. The circular ridge 930 is preferably arranged such that, when properly connected, the ridge contacts (or very nearly contacts) the proximal end 910 of cartridge holder 900. As such, if the stop feature 918 contacts the ridge (and is not inserted into groove feature 930), a gap will remain between the distal end 914 of dose setting mechanism 902 and shoulder 909 of cartridge holder 900. This gap may therefore serve to indicate an incorrect connection to the user.

In a further aspect, any coding feature of the cartridge holder and/or dose setting member may vary in size and shape in one or more planes (e.g., transverse, longitudinal, and/or radial plane). For example, FIG. 10A shows an exemplary collection of stop features having cross-sections 102-112 through a transverse plane, each of which might be used for a different medicament. The cross-section for each drug is larger in one area and smaller in another than for all of the other drugs, which can be seen by overlaying all of the cross-sections in sketch 100. In this way, if the wrong cartridge holder is inserted into the device, the stop will block travel before the holder is fully assembled. FIG. 10B shows another collection of possible coding features having cross-sections 1102-1112, but through the longitudinal plane (i.e. the plane normalized to the curvature of coding feature). The cross-section for each drug is larger in one area and smaller in another than for all of the other drugs, which can be seen by overlaying all of the cross-sections in sketch 1100. A given coding feature might be coded in a transverse plane as in 10A, or it might be coded in a longitudinal plane as in 10B, or both.

Each stop may vary in shape and size. For instance, as shown in FIG. 10A, the stops may vary in radial extent and/or circumferential extent (e.g., stops 102-106 are both radially narrower and circumferentially longer than stops 108-112). The coding features may also vary in axial extent and the edges may vary angularly. For example, as shown, both edges of stop 102 and both edges of stop 108 are normal to the circumference of the coding feature (and thus to the circumference of the outer cylindrical wall of the cartridge holder), while stops 104, 106, 110, and 112 each include one edge that is normal to the circumference, and one edge that is angled relative to the circumference.

In another aspect, coding features may include electro-mechanical verification features; e.g. electrical or optical sensors, microswitches, optical switches, magnetic switches, etc. For example, when a cartridge holder is connected to the correct dose setting member, a switch on an edge of a coding feature (on the cartridge holder and/or the dose setting member) may be triggered. As another example, a sensor on the coding feature of a cartridge holder may be configured to detect a matching sensor on the coding feature of the matching dose setting member. The cartridge-holder sensor may be located so that it only aligns with (and thus detects) the matching sensor on the dose setting member when properly connected. As such, a programmable drug delivery device may be disabled until the switch is triggered or sensors are brought into alignment, helping prevent incorrect administration of medicament.

Applicants' cartridge holders and dose setting members help provide a large number of different coding configurations. Consequently, with proposed coding features, a large number of medicaments can be distinguished from one another. In addition, with Applicants' proposed coding features, if a user attempts to load an incorrect reservoir into a cartridge holder designed for a different cartridge, the user will be alerted at an early stage of the assembly process.

Exemplary embodiments have been described. It should be understood that, in general, the functionality and structural aspects described herein with reference to pin or groove features on a cartridge holder may apply equally with respect to pin or groove features on a dose setting member. Those skilled in the art will understand, however, that changes and modifications may be made to these arrangements without departing from the true scope and spirit of the present invention, which is define by the claims.

The invention claimed is:

1. A cartridge assembly configured to be connected to a dose setting and delivery mechanism, the cartridge assembly comprising:
   a cylindrical body for holding a medicament reservoir, where the cylindrical body has a proximal end portion having an outer surface and an inner surface; a fastener on either the outer surface or the inner surface of the proximal end portion, the fastener being configured to attach the cartridge assembly to the dose setting and delivery mechanism; and
   at least one coding feature that is separate from the fastener, the coding feature being coded to engage a corresponding coding feature on the dose setting and delivery mechanism, thereby allowing the cartridge assembly to operably connect to the dose setting and delivery mechanism,
   where the coding feature is formed as a stop feature and where the corresponding coding feature is formed as a counter stop feature, the stop feature and the counter stop feature being suitable to make contact thereby blocking travel in the connection process and allowing cartridge assembly to operably connect to the dose setting and delivery mechanism;
   wherein the proximal outer surface of the cylindrical body is positioned between a shoulder and a proximal axial end and the fastener is located on the proximal outer surface and where the coding feature of the cartridge assembly is a pin on the proximal outer surface, where the pin abuts, is in contact with, and extends proximally from a proximal facing surface of the shoulder that protects the pin from damage during cartridge assembly.

2. The cartridge assembly of claim 1 where the stop feature is located on the outer surface, or the inner surface, or an axial end of the cylindrical body.

3. The cartridge assembly of claim 1 where the stop feature is configured to contact the counter stop feature in an axial, helical or circumferential direction.

4. The cartridge assembly of claim 3 where the stop feature is configured to contact the counter stop feature in a direction that is normal to the direction of the travel of the cartridge assembly at the time of contact.

5. The cartridge assembly of claim 1 where the coding feature comprises a radial pin.

6. The cartridge assembly of claim 1 where the coding feature comprises an axial pin.

7. The cartridge assembly of claim 6 where the cartridge assembly is configured to be rotated until the pin contacts a counter stop face of a groove feature that is an axial indentation on a circular ridge of the dose setting and delivery mechanism.

8. The cartridge assembly of claim 1 where the fastener is selected from the group consisting of threads, pins and grooves, pins and ridges, bayonet, snap-fit, and detents.

9. The cartridge assembly of claim 1 having an ejection channel configured to accept a fastening pin feature on the dose setting and delivery mechanism when the stop feature and the counter stop feature do not engage, where the fastening pin feature is capable of over-rotating into the ejection channel.

10. A first and a second cartridge assembly of claim 1 where the first cartridge assembly holds a first medicament and the second cartridge assembly holds a second medicament different from the first medicament and where the coding feature of the first cartridge assembly is unique to the first medicament and is specifically coded to engage only a corresponding coding feature on a dose setting and delivery mechanism that is configured to dispense the first medicament and where the second cartridge assembly will not operably connect to the first dose setting and delivery mechanism.

11. The first and second cartridge assemblies of claim 10 where the coding feature of the second cartridge assembly is unique to the second medicament and is specifically coded to engage only a corresponding coding feature on a dose setting and delivery mechanism that is configured to dispense the second medicament.

12. The first and second cartridge assemblies of claim 10 and a third cartridge assembly holding a third medicament different from the first and second medicaments, where the coding feature of the third cartridge assembly is unique to the third medicament and where the third cartridge assembly operably connects only to a third dose setting and delivery mechanism that is different from other dose setting and delivery mechanisms.

13. The first and second cartridge assemblies of claim 10, where the cartridge assemblies have the same type of fasteners, and wherein the coding feature of the first assembly is different from the coding feature of the second assembly.

* * * * *